United States Patent
Arzonico

(10) Patent No.: US 6,626,875 B1
(45) Date of Patent: Sep. 30, 2003

(54) PERSONAL FEMININE HYGIENE DEVICE

(75) Inventor: Jeanne L. Arzonico, Mobile, AL (US)

(73) Assignee: Jeanne Arzonico Bush, Mobile, AL (US)

( * ) Notice: Subject to any disclaimer, the term of this patent is extended or adjusted under 35 U.S.C. 154(b) by 0 days.

(21) Appl. No.: 09/384,731

(22) Filed: Jan. 31, 2003

(51) Int. Cl.$^7$ ............................................. A61M 31/00
(52) U.S. Cl. ...................... 604/279; 604/248; 604/257; 604/264; 604/118
(58) Field of Search ........................ 206/364; 222/566, 222/568, 575, 544, 548, 567, 571, 565; 251/149.2, 149; 239/543, 601, 544, 547; 604/279, 32, 19, 515, 73, 246, 93.01, 248, 257, 264, 275, 39, 118

(56) References Cited

U.S. PATENT DOCUMENTS

| | | | |
|---|---|---|---|
| 3,682,176 A | * 8/1972 | Kelsen .......................... 128/229 |
| 3,754,553 A | * 8/1973 | Hewitt et al. ................. 128/232 |
| 3,782,641 A | * 1/1974 | Springer ...................... 239/598 |
| 3,834,372 A | * 9/1974 | Turney ......................... 128/2 F |
| 4,130,118 A | * 12/1978 | McLaughlin ................. 128/229 |
| 4,248,226 A | * 2/1981 | Pitchford, Jr. ............... 128/229 |
| 4,265,229 A | * 5/1981 | Rice et al. .................... 128/66 |
| 4,309,995 A | * 1/1982 | Sacco .......................... 128/239 |
| 4,324,242 A | * 4/1982 | Cross .......................... 128/232 |
| 4,350,158 A | * 9/1982 | Hudson ....................... 128/224 |
| 4,601,709 A | 7/1986 | Kabbaby | |
| 4,650,470 A | * 3/1987 | Epstein ........................ 604/149 |
| 4,894,053 A | * 1/1990 | Reddick ....................... 604/85 |
| 4,911,704 A | * 3/1990 | Dixon .......................... 604/83 |
| 4,941,872 A | * 7/1990 | Felix et al. ................... 604/27 |
| 5,102,387 A | * 4/1992 | Jorde ........................... 604/39 |
| 5,167,646 A | 12/1992 | Swafford | |
| 5,218,956 A | * 6/1993 | Handler et al. ............... 128/66 |
| 5,241,714 A | * 9/1993 | Barry ........................... 4/605 |
| 5,267,981 A | * 12/1993 | Ducoin et al. ............... 604/275 |
| 5,401,240 A | * 3/1995 | Yang ............................ 604/39 |
| 5,899,878 A | * 5/1999 | Glassman ..................... 604/48 |
| 5,921,970 A | * 7/1999 | Vandenberg ................ 604/264 |
| 6,010,495 A | * 1/2000 | Tilton, Jr. .................... 606/1 |
| 6,156,017 A | * 12/2000 | Shieh .......................... 604/279 |
| 6,190,365 B1 | * 2/2001 | Abbott et al. ............... 604/279 |

* cited by examiner

Primary Examiner—Brian L. Casler
Assistant Examiner—Cris Rodriguez

(57) ABSTRACT

A personal shower hygiene device, in the preferred embodiment is structured so as to allow for douching to occur solely with the use of water. This hygiene device comprises a water coupling device, a flexible hose and a plurality of removable and disposable nozzles. The water-coupling device is connected to the existing water source while the disposable nozzle is coupled to the water-coupling device via the flexible hose. This will enable fluid to flow from the water-coupling device to the nozzle, via the hose, for adequate and efficient douching capabilities. To prevent an excess amount of force from the water, a safety device is provided for limiting the water pressure.

11 Claims, 6 Drawing Sheets

PERSONAL FEMININE HYGIENE DEVICE

BACKGROUND OF THE INVENTION

1. Field of the Invention

The present invention relates generally to a feminine hygiene device, and more particularly to a personal feminine hygiene device which, is attachable to a shower head, either conventional wall mounted shower heads or conventional hand held shower head devices, and that includes removable and disposable nozzles, for inherently providing a device which is sanitary, efficient and adequate for its intended purpose.

2. Description of the Prior Art

Feminine hygiene products, in particular the feminine hygiene products known as douches, have been widely used in the past for vaginal hygiene. Unfortunately, many of these commercially available products tend to contain chemicals, that when used can be irritating to a wide array of consumers. In a normal acidic vaginal environment, the acidic conditions will inherently discourage the growth of yeast and other organisms that can cause infections. In using a douche there exists a chance of changing this normal acidic environment which will innately encourage the growth of yeast and other organisms that can cause infections.

Despite all the negative problems associated with douching, there are some problems, which do require the use of douching. To aid on this end and to provide successful results, several products have been developed to facilitate the process and provide for a more time efficient means of washing. One such device is disclosed in U.S. Pat. No. 5,102,387 issued to Jorde. In this patent there is disclosed a transportable douche attachment which is adapted to be removably secured to a showerhead. To allow for such an attachment, the transportable douche attachment includes a cone that is attachable to the showerhead via a strap. A conventional nozzle, having a plurality of holes, is secured to the opposite end of the cone so as to enable douching to occur. This device, though efficient, does not address the showers, which do not have a flexible showerhead. Most homes include conventional showerheads, which are permanently attached to the stall, and thus, this apparatus would not render successful operation in those environment. In addition, this apparatus fails to disclose a means of controlling water flow, and thus an excess amount of pressure can wash away the plug of mucus that normally covers the cervix and prevents.infectious organisms from getting into the uterus, thereby defeating its intended use.

Yet another device is disclosed in U.S. Pat. No. 5,167,646 issued to Swafford. In this patent there is disclosed a disposable douche means with an adjustable nozzle. This device includes a bag that is attached to the nozzle. For operation, the bag is held or secured to a wall in an upward position. This will allow for gravity to control the fluid flow through a tube to the nozzle. Though somewhat efficient, attaching the bag to a convenient place may be cumbersome, while the elongated shape of the nozzle may be uncomfortable to control, manipulate and utilize. In addition, since there is no means to control water flow, there exists the chance for excess fluid pressure, inherently forcing vaginal organisms into the uterus, where they can cause an infection.

Still another device is disclosed in U.S. Pat. No. 4,601,709 issued to Kabbaby. In this patent there is disclosed a shower-mounted douche apparatus having a portion mountable between the water source and the showerhead. A hose couples the water source to a nozzle. Sandwiched between the nozzle and the water source is a mixing chamber for maintaining the medicine therein and for allowing the water to mix with the medicine:for producing a solution. Though efficient in operation, this device is complex and may be difficult to use, even for the typical consumer. In addition excess use of chemicals by the user can be detrimental and may, in fact, cause infections and the like to due to the acidic change in the vaginal environment.

Accordingly, it is seen that what is needed is a douche apparatus which is efficient in use and which does not exert an excess amount of pressure for use. This product should be easy to use and include removable and disposable nozzles, which provide an inherent sanitary apparatus. Further still, there is a tremendous need for a product which does not encourage the use of chemicals for douching, but one which may be adapted to accept a chemical solution should the need arise and as directed by a physician.

As will be seen, the present invention achieves its intended purposes, objectives and advantages, by accomplishing the needs as identified above, through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention is a personal shower hygiene device, which is designed, and configured to allow douching to occur without the discomforts and problems generally associated with the process. In the preferred embodiment, the personal shower hygiene device of the present invention is structured so as to allow for douching to occur solely with the use of water.

To enable such an environment and arrangement, the present invention, in a first embodiment, comprises a water coupling device, a flexible hose and a plurality of removable and disposable nozzles. Each element and component of the present invention is formed for ultimate comfort and ease in usability for the consumer. The water-coupling device is connected to the existing water source while the disposable nozzle is coupled to the water-coupling device via the flexible hose. This will enable fluid to flow from the water-coupling device to the nozzle, via the hose, for adequate and efficient douching capabilities. This first embodiment is ideal for use with wall mounted showerheads.

For flexible showerheads, also known as hand-held showerheads, a hose is already provided. In this configuration the nozzle is removable attached to the showerhead via an attaching device. Once the nozzle is attached, douching can occur adequately.

In the first embodiment, the water-coupling device is a device that is sandwiched between the showerhead and the water source. This water-coupling device includes a valve, which enables the user to select either the use of the showerhead or, optionally, the use of the present invention. By providing a device that is coupled to the existing water source of the home will innately provide a device that permits the water to be at a comfortable and a temperature controlled state. This is a condition that is desirable by the consumer.

Alternatively, this valve can include a pressure altering means, which is conventional, for allowing the user the option of providing the particular and desired pressure needed for adequate cleaning. This will provide a device, which is adjustable and customized to the user's wishes.

In yet another alternative arrangement, the valve can include the option for receiving air. The air introduced within the valve will initiate turbulence. This turbulent water flow will exit the nozzle. Offering yet another option for adequate cleansing.

It is noted that the valve can include an aperture that will allow water to flow at a certain pressure. This is an optional safety measure and is solely designed so as to eliminate the possibility for an excess amount of force from the water to be introduced into the vaginal environment. This safety measure will prevent the removal of the plug of mucus that normally covers the cervix and prevents infectious organisms from getting into the uterus.

Another means of controlling the force of water flow is to provide for a washer to be located between the hose and showerhead. The orifice within the washer will be of a diameter, which will control water pressure through the hose, and out the nozzle. Such an arrangement is a safety measure and will enable reliable operation of the nozzle of the present invention and without the possibility of harm to occur with the user.

The hose is a flexible element that is easy to use and to manipulate. This flexible hose will couple the nozzle to the water source, and thus, carry the water from the source to the nozzle. The hose includes a first end and a second end. The first end is connected to the water coupling device via conventional means, such as, but not limited to threaded attachments, snap on means, and the like. The second end, like the first end, is coupled to the nozzle via conventional means. This second end includes a means for easily and quickly removing and disregarding the nozzle. This will provide for the nozzle to be removably secured to the second end of the hose. Hence, the removing means is any conventionally utilized device which can produce successful and quick results, such as threadably attaching the nozzle to the hose, snapping the nozzle to the hose, or the like.

For douching, a nozzle is provided. This nozzle is disposable and thus, for each use a new nozzle will be removably secured to the second end of the hose. Each nozzle will be fabricated from a lightweight, yet durable material. Each douche is designed and configured substantially the same and includes unique features. The nozzle comprises a shaft. Angularly secured to the shaft is a second shaft. This first shaft and second shaft are integral, and the second shaft is secured to the first shaft at an obtuse angle. This will innately allow for comfortable insertion into the vaginal area.

Extending through the second shaft is a plurality of apertures. These apertures enable water to flow therethrough. For controlling the water flow, and for optimizing the cleaning potential, without compromising the health issues, these apertures can include different configuration.

One configuration provides the holes to be tapered downward into the hollow interior of the nozzle for providing the openings within the nozzle to be smaller than the openings for exiting the nozzle. This will reduce the water pressure exiting the nozzle. For increase pressure, the holes can be tapered outward to provide for the openings within the nozzle to be larger than the openings for exiting the nozzle. Alternatively, these openings can include any geometric shape for alternating the desired fluid flow.

In an alternative embodiment, the nozzle can include a chamber for receiving medicine, as prescribed by a physician. In this arrangement, the medicine will be mixed with water to allow for the solution to be dispensed according.

A clip is also included and this clip is designed to be attached to a wall and for maintaining the plurality of nozzles. This clip will enable the maintenance of the apparatus when not in use. When desired to use the present invention, it can easily and quickly be removed from the clip.

In the second embodiment, the nozzle, as described above, can be attached directly to the showerhead, such as conventional hand-held devices, via an attaching device. The attaching device can include a valve device, medicine chamber and/or washer as described above, so as to provide for a device which can be successfully utilized when desired.

Accordingly, it is the object of the present invention to provide for a disposable douche, which will overcome the deficiencies, shortcomings, and drawbacks of prior douches and methods of douching thereof.

Another object of the present invention is to provide for an douche assembly which includes disposable nozzles and one which utilizes water for douching, yet alternatively provides a means for the introduction of medicine.

A further object of the present invention, to be specifically enumerated herein, is to provide a douche assembly in accordance with the preceding objects and which will conform to conventional forms of manufacture, be of simple construction and easy to use so as to provide a device that would be economically feasible, long lasting and relatively trouble free in operation.

Although there have been many inventions related to a douche apparatus, none of the inventions have become sufficiently compact, low cost, and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

FIG. 1a is an exploded perspective view of various components used with the personal feminine hygiene device of the present invention used with a typical and conventional shower head generally used by individuals in homes and the like.

FIG. 1b is an exploded perspective view of various components used with the personal feminine hygiene device of the present invention, illustrating a hose including ends having different attaching mechanism attached thereto and utilized with a typical and conventional shower head generally used by individuals in homes and the like.

Similar reference numerals refer to similar parts throughout the several views of the drawings.

DESCRIPTION OF THE PREFERRED EMBODIMENTS

Figure 1A:
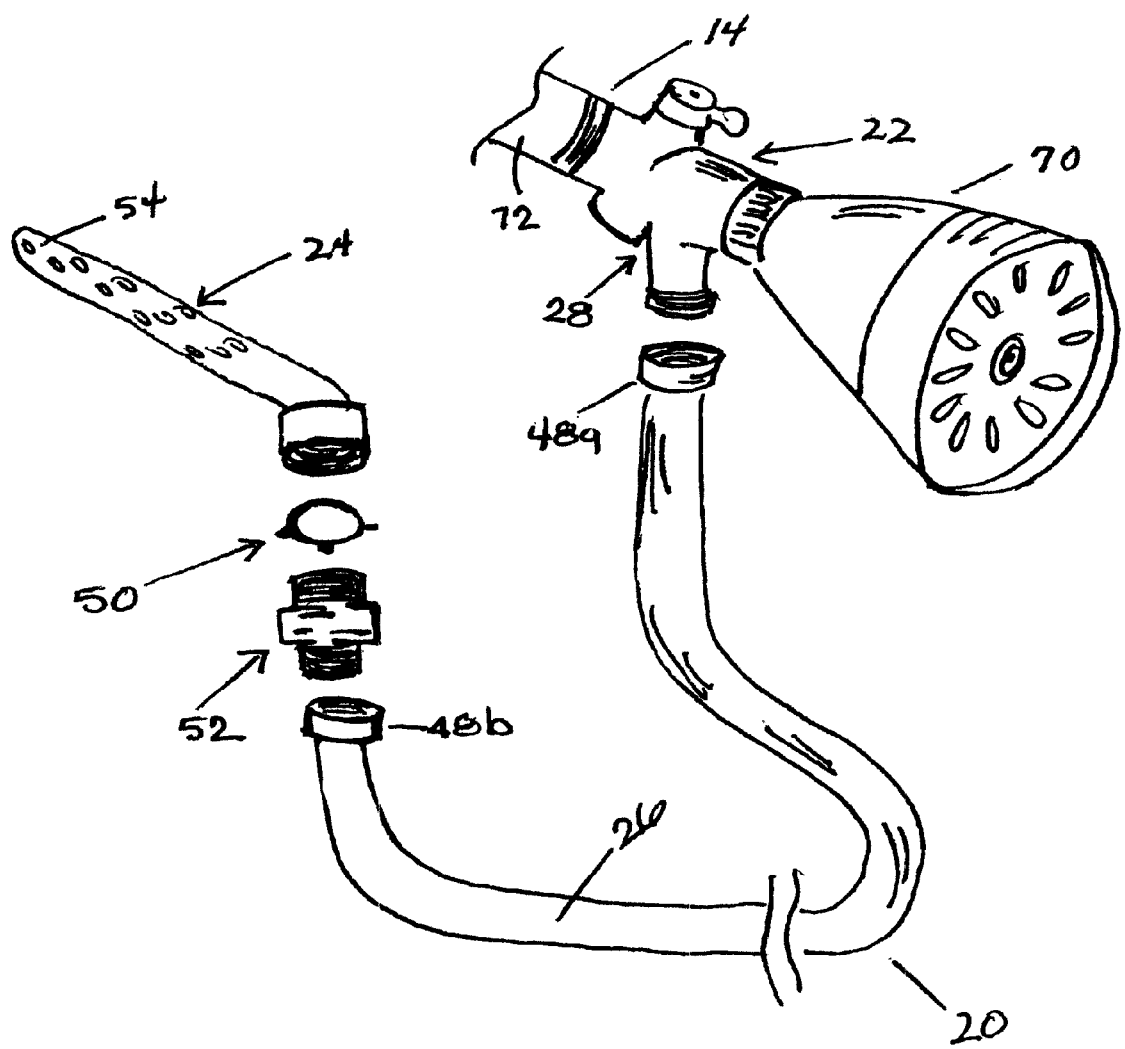
Figure 1B:
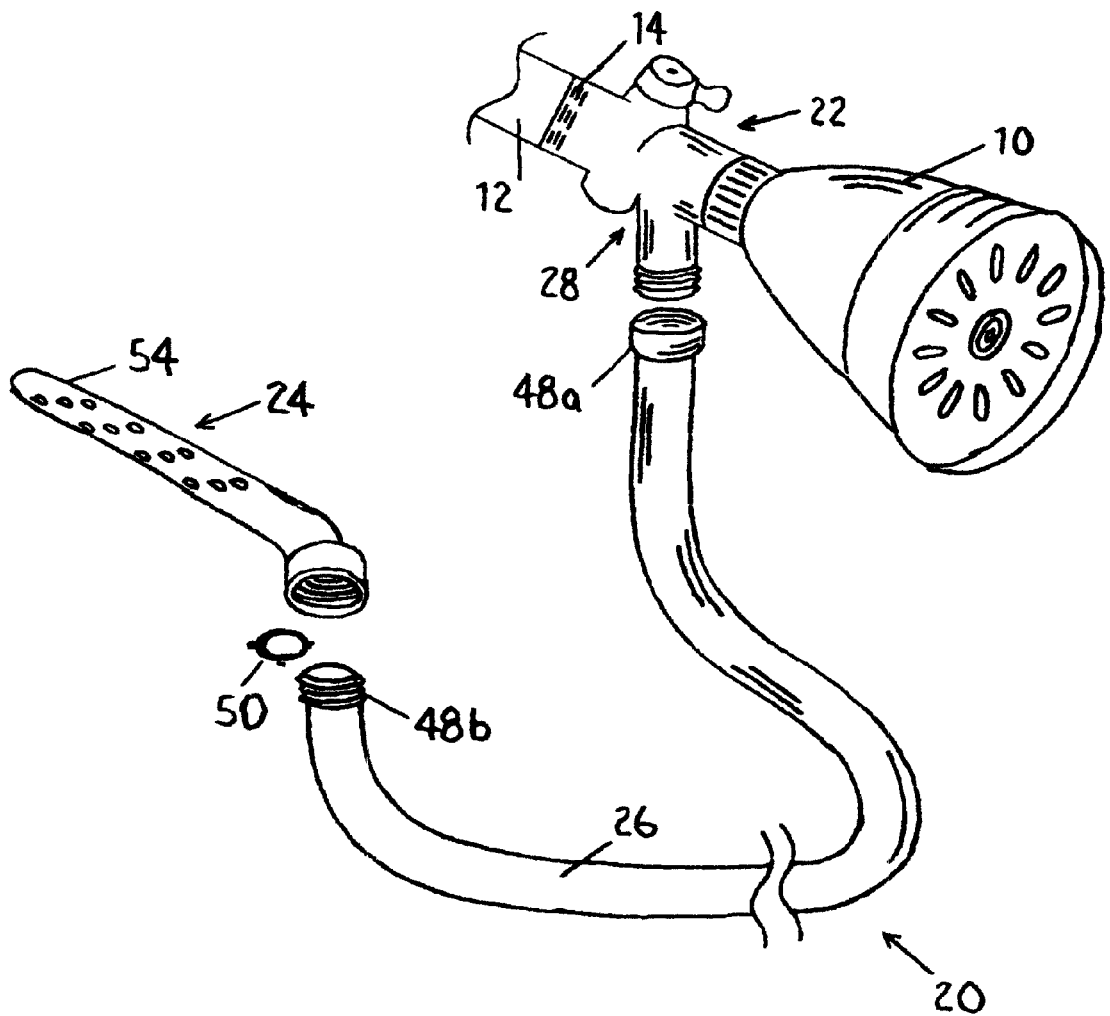

As seen in the drawings, in particular to FIG. 1a and FIG. 1b there is shown a personal feminine hygiene device, denoted by reference numeral 20, which is designed and configured to be removably secured to a conventional shower head, such as the one illustrated in FIG. 1a and FIG. 1b.

Briefly, conventional showerheads 10, as seen by the example of one illustrated in FIG. 1a and FIG. 1b, are removably secured to a pipe 12. This pipe 12 protrudes outward from the wall and enables connecting the showerhead to the water source of the home. To permit the resident to change, remove and/or replace the showerhead 10, conventional attaching mechanisms are utilized. As seen in FIG. 1a and FIG. 1b, the most common is to have a threaded male extension 14 (illustrated in outline) extending outwardly from the pipe 12. The showerhead will include a female internally threaded receiving mechanism (not illustrated) for receiving and securing the showerhead 10 to the pipe 12. Thereby, the user can merely unscrew the showerhead when desired.

The present invention is a feminine hygiene device, which is structured so as to be provide for douching to occur in one's shower. This will provide for the present invention 20 to include a first end and a second end. One end is sandwiched between the pipe 12 and the head 10 while the second end includes a disposable douche.

Since one end will be secured between the pipe and showerhead, this end will inherently provide for the present invention to be coupled to a water source. Coupling to a water source will allow for douching to occur without the discomforts and problems generally associated with the process.

To enable such an arrangement, the present invention 20, as seen in FIGS. 1a–3, includes first end 22 and a second end 24. The first end 22 is designed and configured to be coupled to the water source of a conventional home. Hence, this first end 22 of the present invention will be coupled to the pipe 12. The second end 24 includes a disposable nozzle device, which is used in the douching process. Coupling the first end 22 to the second end 24 is flexible and resilient hose or tubing 26.

Located at the first end 22 is a valve assembly 28. The valve assembly is illustrated in FIG. 1a and FIG 1b. As seen, this valve assembly 28 will be located between the pipe 12 (illustrated in FIGS. 1a and 1b) and the shower head 10 (illustrated in FIGS. 1a and 1b) to inherently provide for the valve to act as a water coupling device.

Figure 2:
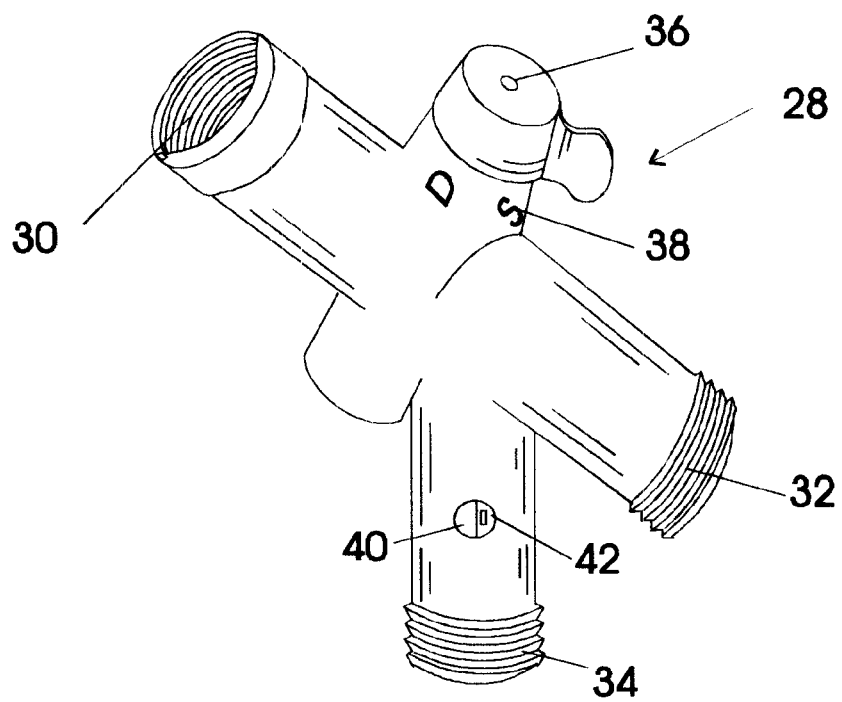
FIG. 2 is an enlarge view of the valve assembly used with the personal hygiene device of the present invention.

This water coupling device or valve assembly 28 includes a first receiving end 30 and a second receiving end 32. The first receiving end is for receiving the conventional pipe. This first receiving end 30, as seen in FIG. 2, is an internally threaded end. The second receiving end 32 is a male protruding externally threaded portion and is designed to receive the conventional showerhead.

Extending downwardly from the water-coupling device 28 is a third receiving member 34. Hence, it is seen that the first receiving end 30 is an inlet for water, while the second and third receiving ends are outlets. Accordingly, water flows into the valve assembly via the inlet 30. The water can flow out via outlet 32 or optionally outlet 34.

This second outlet or the third receiving member receives the tubing 26. Thus the water can flow out the showerhead 10 or optionally flow into the tubing 26.

Internally located within the water-coupling device 28 is a conventional valve having a handle 36 secured thereto. This valve is conventional and enables the user to select either the use of the showerhead or, optionally, the use of the present invention, via the handle 36. When selecting the shower end, the handle 36 is rotated so that the second receiving end 32 will be opened while the third receiving end will be blocked. This will allow for water to flow from the pipe through the valve assembly and out the showerhead. Selecting the present invention, the handle 36 is rotated to a second position so as to allow for the third receiving end 34 to be opened while the second receiving end will be blocked. This will allow for water to flow from the pipe through the valve assembly and out the third receiving end through the tubing 26, for ultimately allowing douching to occur. To ease in the selection, indicias, 38 can be located on the exterior of the valve assembly 28. This will provide a visual means of illustrating which option has been selected.

By providing a device that is coupled to the existing water source of the home will innately provide a device that permits the water to be at a comfortable, partially heated, temperature. This is a condition that is often desirable by the consumer. In addition, since the device is coupled to the user's water source, she can also select the desired pressure while douching. However, many individuals will not realize that excess pressure during douching can be harmful and dangerous. Accordingly, the present invention will include a maximum aperture (opening) between the water source and the third receiving means that will allow water to flow at a certain pressure. This is a safety measure and is solely designed so as to eliminate the possibility of excess water force to be introduced into the vaginal environment. This safety measure will prevent the removal of the plug of mucus that normally covers the cervix and prevents infectious organisms from getting into the uterus.

For convenience, alternating the pressure can also occur via the valve assembly as opposed to alternating via the water source. In this configuration, the valve assembly can include means for reducing the size of the opening between the water source and the third receiving end 34 for alternating the pressure. This alternating means will occur via the handle. Thus, as the user rotates the handle, the opening between the third receiving end 34 and the water source is changed for innately changing the pressure.

Optionally, the valve assembly 28 can further include an aperture 40 extending therethrough and in the path of the third receiving end 34. This aperture 40 will extend from the exterior of the assembly to the pathway of the water and will include a cover 42 (partially illustrated). This will enable the user to select the option of opening or closing this aperture when the douche is selected via the valve. Exposing the aperture (removing or sliding the cover) will introduce air into the assembly will provide a slight amount of turbulence.

Another safety measure is to provide for a safety washer 44, as seen in FIGS. 1a–3. This safety washer will be located between the hose and the valve assembly 28. This washer will include an orifice 46 of a certain diameter, which will control the pressure, and force of the water flow from the water source. This will prevent excess pressure and force, and thus this washer is a safety and precautionary device. Preferably, the orifice will have a diameter in the range of approximately ½ of an inch to ⅛ of an inch. These are the ranges of the diameters which have been used to produce favorable results. It is noted that these diameter can vary slightly, as deemed necessary by the manufacturer.

The tubing 26 is conventional hose material, which is flexible so as to provide a device, which is easy to use and manipulate. The tubing or hose 26 includes opposite ends 48a and 48b, respectively, having conventional male and female coupling devices attached thereto as seen in FIG. 1b. These conventional coupling devices can threadably attach the hose to the valve assembly 28 and douche assembly, as seen, or optionally snapping the hose ends to the respective valve assembly and nozzle.

The coupling device used at the second end of the hose 26 is to enable quick and easy removal of the disposable nozzle. After each use, the nozzle is removed and prior to each use, a new nozzle is attached thereto. The use of disposable nozzles provides a device that is sanitary and convenient.

Figure 5:
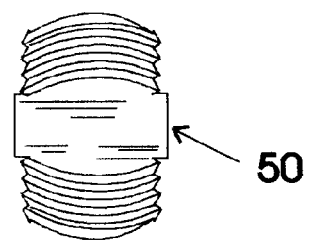
FIG. 5 is an alternative arrangement of a connecting device that can be used with the personal hygiene device of the present invention.

To reduce leakage, a washer 50 can be located between the nozzle and second end 48b of the hose 26. Optionally, in cases where each hose includes female-receiving ends, as seen in FIG. 1b, a double male adapter 52, as seen in FIG. 5, can be used. This will enable the attachment of the nozzle to the second end 48b of hose 26 via male adapter 52.

Figure 4A:
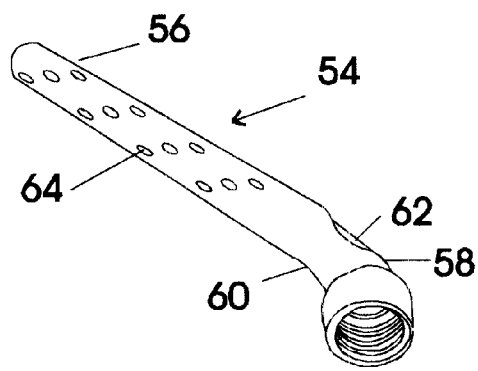
FIG. 4a is an enlarged front view of the nozzle that is used with the personal hygiene device of the present invention.
Figure 4B:
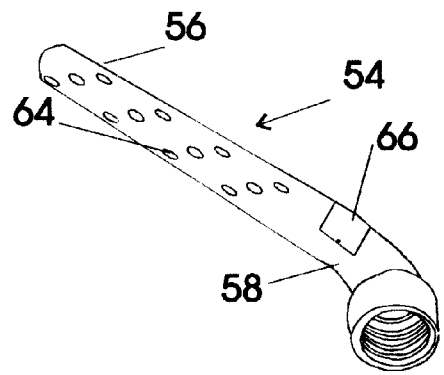
FIG. 4b is an enlarged rear view of the nozzle that is used with the personal hygiene device of the present invention.
Figure 4C:
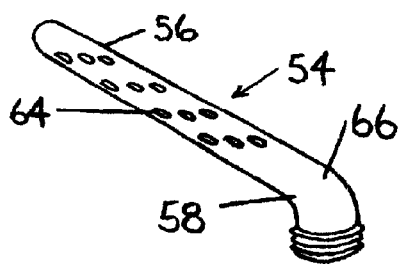
FIG. 4c is an enlarged rear view of the nozzle that is used with the personal hygiene device of the present invention, illustrating an external threaded attaching mechanism.

For douching to occur, the nozzle 54 is provided, as seen in FIGS. 1, 4a, 4b and 4c. This nozzle is disposable and thus for each use, a new nozzle will be removably secured to the second end of the hose. Thereby, a plurality of nozzles will be provided within each apparatus of the present invention. Each nozzle will be substantially the same shape and configuration, and thus, only one nozzle is illustrated for description. Accordingly, as seen, each nozzle is hollow in structure and includes a top section 56 and a lower section 58. The lower section 58 includes the attaching device for attaching the nozzle to the second end of the hose. This attaching device, as seen in FIGS. 4a and 4b can be internally threaded or can be externally threaded as seen in FIG. 4c. Extending upwardly from the attaching device is a shaft 60. Located on the shaft is an indented portion 62. This portion is a finger grip section and is designed to comfortably receive the thumb of the user and to allow for easy and quick removal and/or attachment of the nozzle to hose 26.

Angularly secured to the shaft 60 is the second or top section 56. This top section, preferably, is slightly tapered, as seen, to provide for the lower area to be larger in circumference than the upper-area. This will consequently provide for a more comfortable fit. The tip of the upper area can be opened, as seen in FIG. 4b.

The attachment between the shaft 60 to the top section 56 occurs at an acute angle. Thus with respect to the shaft, the angle occurs between approximately 10–60 degrees, but preferably occurs at 35 degrees. The attachment between the first shaft and top section are integral, and thus provides for an integral nozzle.

Extending through the top section is a plurality of apertures or slits 64. These apertures or slits 64 enable water to flow therethrough as well as the open top end of the upper area. For controlling the water flow, and for optimizing the cleaning potential, without compromising the health issues, these apertures or slits can include different configuration.

Figure 10A:
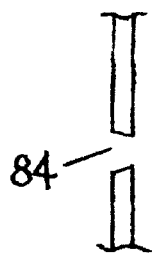
FIG. 10a is a partial cross sectional view of a nozzle illustrated a tapered inward opening.
Figure 10B:
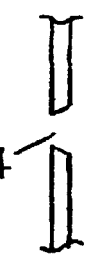
FIG. 10b is a partial cross sectional view of a nozzle illustrated a tapered outward opening.
Figure 7:
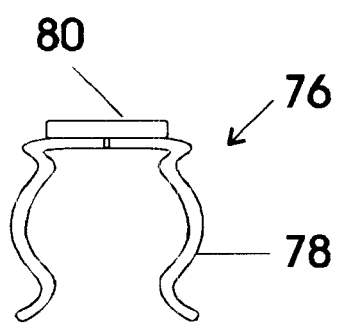
FIG. 7 is a top view of the retaining device used to retain the hose when the personal hygiene device is not in use.

One configuration provides the holes 84 to be tapered downward as seen in FIG. 10a into the hollow interior of the nozzle for providing the openings within the nozzle to be smaller than the openings for exiting the nozzle. This will reduce the water pressure exiting the nozzle. For increase pressure, the holes 84 can be tapered outward as seen in FIG. 10b to provided for the openings within the nozzle to be larger than the openings for exiting the nozzle. Alternatively, these openings can include any geometric shape for alternating the desired fluid flow.

Preferably, the holes extending through the nozzles are arranged in a spiral configuration. This will enable water to be dispersed in smooth and even fashion, as seen by the directional arrows located on FIG. 1. The disbursement will render a comfortable flow of water within the vaginal environment.

In an alternative embodiment, as seen in FIG. 4b, the nozzle can include a chamber 66 for receiving medicine, as prescribed by a physician. In this arrangement, chamber will include a door, exteriorly located. The door is opened to reveal the chamber and to allow for the medicine to be located therein. Once located therein, the water will mix with the medicine, and thus a solution is formed. The formed solution will exit the nozzle via the holes 64 for adequate dispensing.

Figure 6:
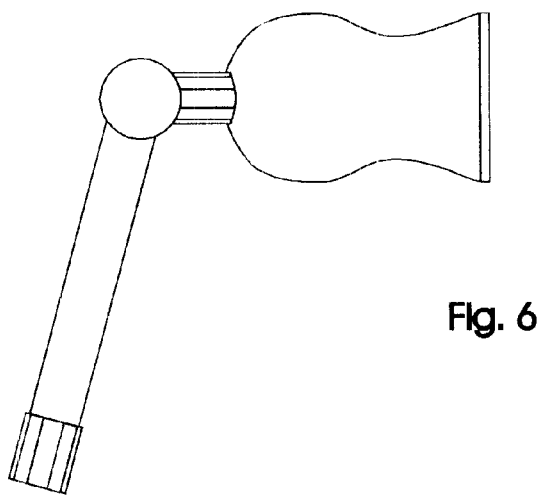
FIG. 6 is an alternative embodiment of the personal hygiene device used with a hand held showerhead of the present invention.

For hand held shower heads, an adapter can be used to couple the showerhead to the nozzle 54 of the present invention. An example of such a device is illustrated in FIG. 6. As seen, this adapter 68 includes an attaching device 70. The attaching device can include two separate configurations. In the first configuration, this attaching device as seen in FIG. 6, will include a resilient seal that is hollow. This will provide for the seal to be a hollow cylindrical member having an opened end for receiving the conventional showerhead. The use of resilient material will enable the open end to be widen and stretch for attachment to the head. Once located thereon, the seal will return to its original size and thus will be snugly located on the showerhead. In this first configuration, the seal is located over the showerhead.

In the second configuration, the attaching device can be located within the showerhead. In this design the attaching device will include conventional threadable members that are adapted to be located within the interior area of the showerhead. This will allow for the attaching device 70 to be located interiorly to the showerhead.

Figure 3:
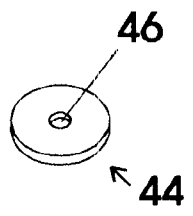
FIG. 3 is an exploded view of the safety washer used with the personal hygiene device of the present invention.

In either configuration, secured to this attaching device the attaching member 72. This attaching member includes an internal channel 74 (illustrated in outline) that enables water to flow from the showerhead to the outlet 76. The outlet includes a connecting means for connection the nozzle to the attaching member 72. Located within the channel is the safety washer 44, as described in the first embodiment and as illustrated in FIG. 3. Optionally, a chamber 66 can be located in this attaching member.

To maintain the hose 26 and/or nozzle in a stored position, a clip 76 is provided. This clip includes a front portion and a rear portion. The front includes a pair of resilient arms 78 having a gap located there between. The gap receives the nozzle or hose, while the arms fictionally maintain it in a fixed and secured position. The rear portion includes an adhesive mountable pad 80 for allowing the clip to be secured to a particular surface, such as a wall or the like.

Figure 8:
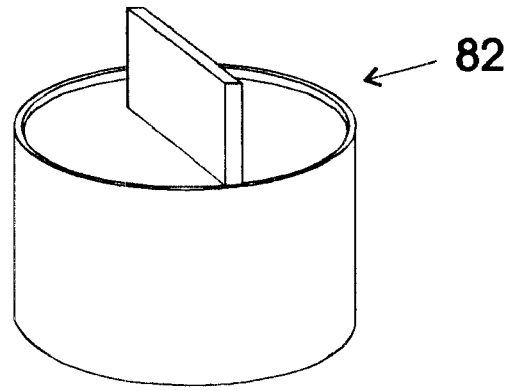
FIG. 8 is a side view of an end cap that is removably secured to the hose and-is attached when the personal hygiene device is not in use.

When the device is not in use and the nozzle is removed therefrom, it may be desired to enclosed the second end of the hose 26. To enable closure, an end cap 82, illustrated in FIG. 8 is provided. This end cap 82 is a hollow container body having an enclosed top and an opened bottom. The open bottom includes receiving means that correspond to the receiving end of the second end of the hose. Hence, in the examples provided, the open end includes internally threaded member. This will allow for the end cap to easily and quickly secure to the hose.

Figure 9:
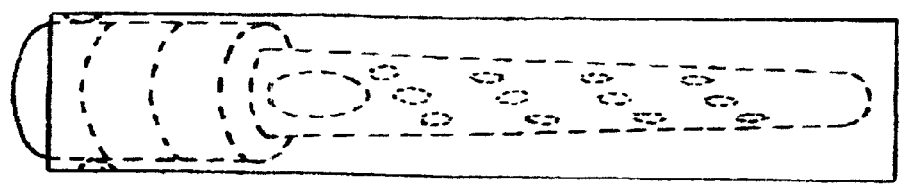
FIG. 9 is a side view of a container storing a plurality of nozzles that is used with personal hygiene device of the present invention.

For maintaining the disposable nozzles, a container 86 as seen in FIG. 9 is utilized. This container can include any shape or designed, as deemed necessary by the manufacture. The object of this container is to store and maintain the other nozzles when not in use. This container, like the clip, can be mounted to the wall, or optionally, can be a free standing structure.

While the invention has been particularly shown and described with reference to an embodiment thereof, it will be understood by those skilled in the art that various changes in form and detail may be made without departing from the spirit and scope of the invention.

I claim:

1. A disposable douche assembly adapted to be removably secured to an existing shower, said disposable douche assembly consisting of:
   a first end and a second end;
   a valve assembly removably secured to an existing water source of a home and said valve assembly is located at said first end;
      said valve assembly includes a first position and a second position;
   a disposable nozzle coupled: to said valve assembly via a hose;
      said disposable nozzle is located at said second end and includes a plurality of apertures for enabling water to flow therethrough;
      said nozzle includes a top portion and a lower portion and said top portion is integral with said lower portion and forms a singular unit;
      said top portion includes said plurality of apertures, said top portion is secured to said lower portion at an acute angle;
      said plurality of apertures is located circumfercially and in a spiral configuration around said nozzle;
   an attaching device enables said disposable nozzle to be removably secured to said hose said plurality of apertures is tapered inward;
   a safety device sandwiched between said valve assembly and said disposable nozzle, said safety device controls pressure from said water source to said disposable nozzle; and
   said first position of said valve assembly enables normal operation of said existing water source at a shower and said second position disables water flow to said shower and enables water to flow to said nozzle, a double male adapter means for removably securing the nozzle to the adapter means and further including a washer located between the adapter means and the hose, said adapter means and said washer being attached to the hose to reduce leakage in the assembly.

2. A disposable douche assembly as in claim 1 wherein a plurality of nozzles are provided, each nozzle includes substantially same shape and configuration, said nozzles being disposable after each use.

3. A disposable douche assembly as in claim 2 wherein said plurality of nozzles, are maintained via a container.

4. A disposable douche assembly as in claim 1 wherein a clip maintains said hose when not in use, said clip includes a back surface and a front surface, said back surface includes an attaching element for attaching to a desired surface, said front surface includes receiving element for enabling said receiving element to receive and maintain said hose.

5. A disposable douche assembly as in claim 1 wherein said lower portion includes an indented area for receiving a thumb of a user.

6. A disposable douche assembly as in claim 1 wherein an end cap is removable secured to said hose, said end cap is secured to said hose once said nozzle is removed and disposed.

7. A disposable douche assembly as in claim 1 wherein said valve assembly includes an inlet, a first outlet and a second outlet, said inlet is secured to said water source, first outlet is secured to an existing shower head, said second outlet is secured to said hose, said safety device is a washer and is located between said second outlet and said hose.

8. A disposable douche assembly as in claim 1 wherein said valve assembly is controlled via a handle and indicia are exteriorly located on said valve assembly for indicating outlet selected.

9. A disposable douche assembly as in claim 1 wherein said nozzle includes a chamber for receiving medicine for allowing said medicine mix with water for forming a solution and to exit via said nozzle.

10. A disposable douche as in claim 1 wherein said hose includes outer ends and each end includes an internally threaded member, said internally threaded member constitutes said attaching device and said nozzle includes externally threaded member and said valve assembly includes externally threaded member.

11. A disposable douche as in claim 1 wherein said nozzle includes a tip and said tip includes an opening.

* * * * *